(12) United States Patent
Hodges et al.

(10) Patent No.: US 6,174,420 B1
(45) Date of Patent: Jan. 16, 2001

(54) ELECTROCHEMICAL CELL

(75) Inventors: Alastair McIndoe Hodges, Blackburn South Victoria; Thomas William Beck, South Windsor; Oddvar Johansen, Mulgrave; Ian Andrew Maxwell, Leichhardt, all of (AU)

(73) Assignee: USF Filtration and Separations Group, Inc., Timonium, MD (US)

( * ) Notice: Under 35 U.S.C. 154(b), the term of this patent shall be extended for 0 days.

(21) Appl. No.: 09/314,251

(22) Filed: May 18, 1999

Related U.S. Application Data

(63) Continuation of application No. 09/068,828, filed on Mar. 15, 1999, and a continuation of application No. 08/852,804, filed on May 7, 1997, now Pat. No. 5,942,102.

(30) Foreign Application Priority Data

Nov. 15, 1996 (WO) .................................. PCT/AU96/00723

(51) Int. Cl.[7] .................................................. G01N 27/26
(52) U.S. Cl. ............................................ 204/403; 204/409
(58) Field of Search ..................................... 204/403, 409, 204/411; 324/450

(56) References Cited

U.S. PATENT DOCUMENTS

| | | | |
|---|---|---|---|
| 5,312,590 | * 5/1994 | Gunasingham | 422/56 |
| 5,437,999 | * 8/1995 | Diebold et al. | 435/287.9 |
| 5,520,787 | * 5/1996 | Hanagan et al. | 204/409 |
| 5,997,817 | * 12/1999 | Crismore et al. | 422/58 |

* cited by examiner

Primary Examiner—Jill Warden
Assistant Examiner—Alex Noguerola
(74) Attorney, Agent, or Firm—Knobbe, Martens, Olson and Bear, LLP

(57) ABSTRACT

A method of manufacture of a thin layer electrochemical cell (FIGS. 12, 14) comprising the steps of:

forming an aperture (11) extending through a sheet (1) of electrically resistive material, said aperture defining a side wall of the cell, mounting a first thin electrode layer (13) to one side of the sheet and extending over aperture (11) whereby to define a cell first end wall, mounting a second thin electrode layer (13) to the other side of the sheet and extending over aperture (11) whereby to define a second cell end wall in substantial overlying registration with the first electrode, and providing means (16) for admission of a liquid into the cell.

8 Claims, 3 Drawing Sheets

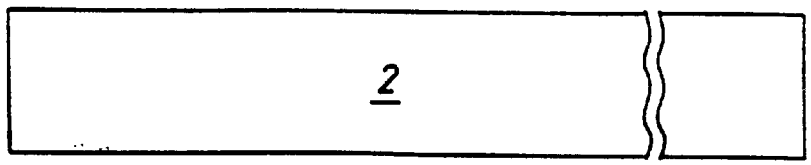
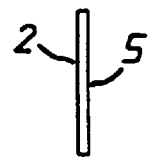
FIG.1  FIG.3
FIG.2
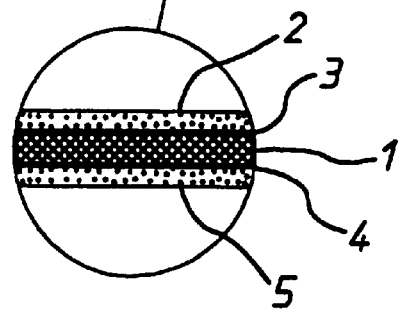
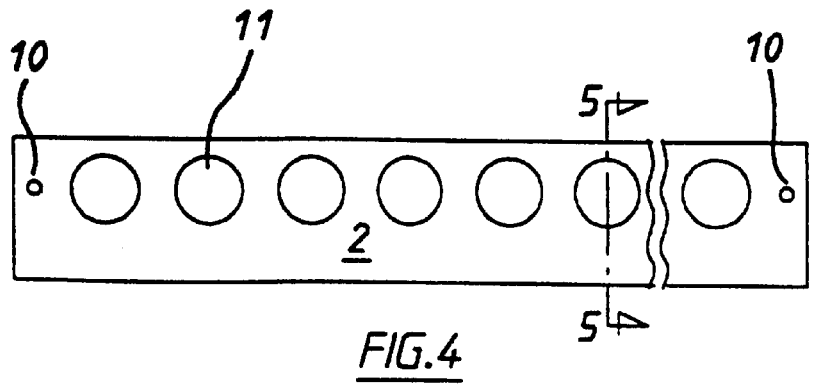
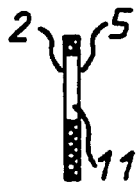
FIG.4  FIG.5

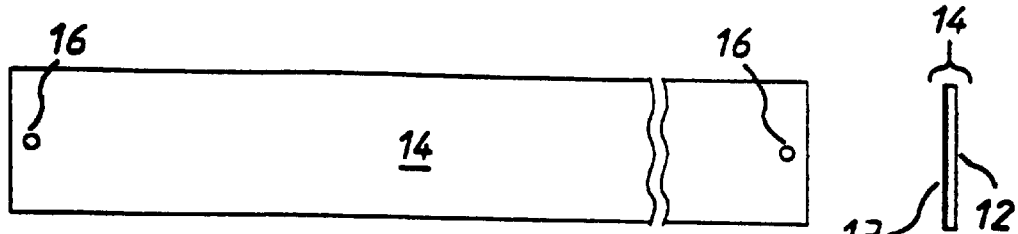
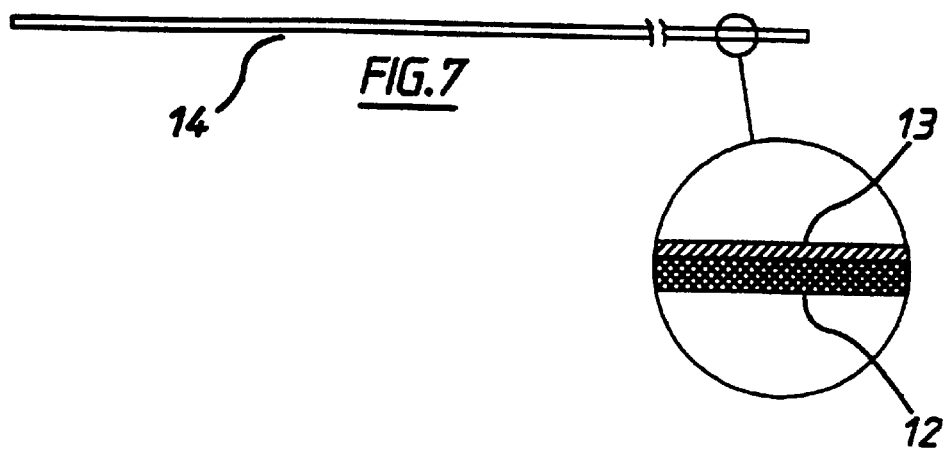
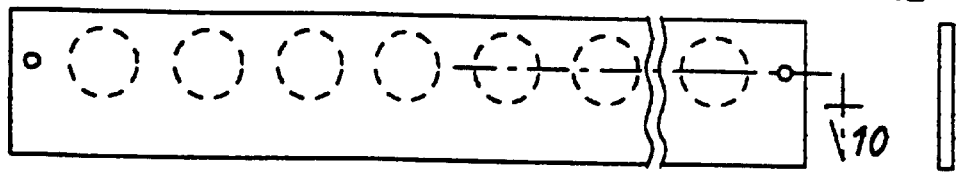
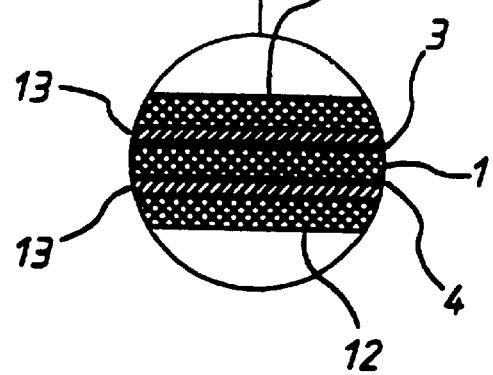

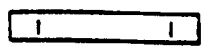
FIG. 13
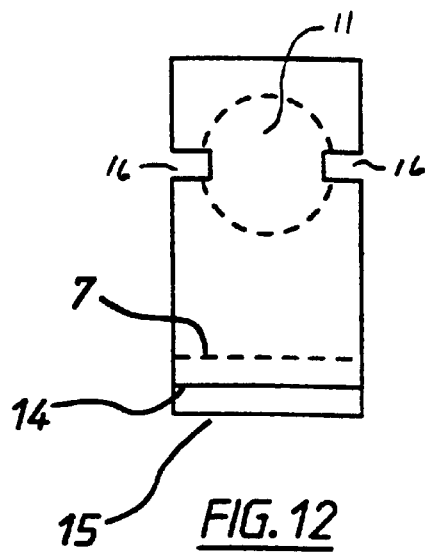
FIG. 12
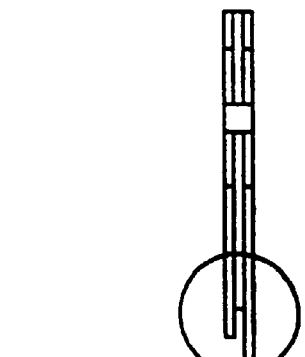
FIG. 14
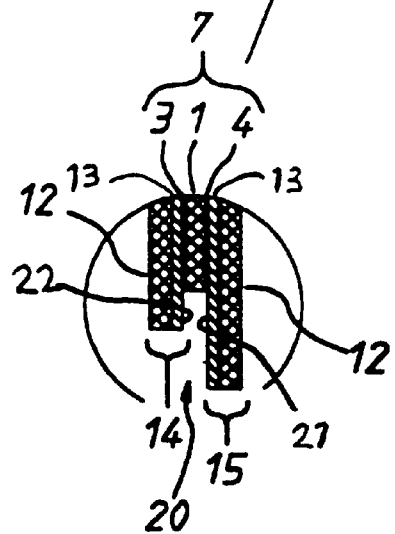
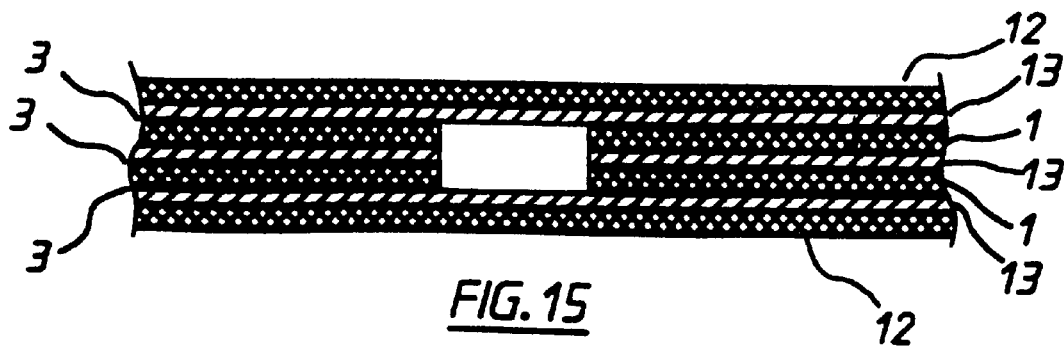
FIG. 15

ELECTROCHEMICAL CELL

FIELD OF THE INVENTION

This invention relates to an electrochemical cell for determining the concentration of an analyte in a carrier. This application is a continuation of U.S. application Ser. No. 09/068,828, entitled ELECTROCHEMICAL CELL, filed on Mar. 15, 1999, and of U.S. application Ser. No. 08/852,804, entitled ELECTROCHEMICAL METHOD, filed on May 7, 1997 U.S. Pat. No. 5,942,102, the contents of which are incorporated herein by reference.

BACKGROUND ART

The invention herein described is an improvement in or modification of the invention described in our co-pending U.S. application Ser. No. 08/981,385, entitled ELECTROCHEMICAL CELL, filed on Dec. 18, 1997, the contents of which are incorporated herein by reference.

The invention will herein be described with particular reference to a biosensor adapted to measure the concentration of glucose in blood, but it will be understood not to be limited to that particular use and is applicable to other analytic determinations.

It is known to measure the concentration of a component to be analysed in an aqueous liquid sample by placing the sample into a reaction zone in an electrochemical cell comprising two electrodes having an impedance which renders them suitable for amperometric measurement. The component to be analysed is allowed to react directly or indirectly with a redox reagent whereby to form an oxidisable (or reducible) substance in an amount corresponding to the concentration of the component to be analysed. The quantity of the oxidisable (or reducible) substance present is then estimated electrochemically. Generally this method requires sufficient separation of the electrodes so that electrolysis products at one electrode cannot reach the other electrode and interfere with the processes at the other electrode during the period of measurement.

In our co-pending application we described a novel method for determining the concentration of the reduced (or oxidised) form of a redox species in an electrochemical cell of the kind comprising a working electrode and a counter (or counter/reference) electrode spaced from the working electrode by a predetermined distance. The method involves applying an electric potential difference between the electrodes and selecting the potential of the working electrode such that the rate of electro-oxidation of the reduced form of the species (or of electro-reduction of the oxidised form) is diffusion controlled. The spacing between the working electrode and the counter electrode is selected so that reaction products from the counter electrode arrive at the working electrode. By determining the current as a function of time after application of the potential and prior to achievement of a steady state current and then estimating the magnitude of the steady state current, the method previously described allows the diffusion coefficient and/or the concentration of the reduced (or oxidised) form of the species to be estimated.

Our co-pending application exemplifies this method with reference to use of a "thin layer electrochemical cell" employing a GOD/Ferrocyanide system. As herein used, the term "thin layer electrochemical cell" refers to a cell having closely spaced electrodes such that reaction product from the counter electrode arrives at the working electrode. In practice, the separation of electrodes in such a cell for measuring glucose in blood will be less than 500 microns, and preferably less than 200 microns.

The chemistry used in the exemplified electrochemical cell is as follows:

glucose+GOD→gluconic acid+GOD*  reaction 1

GOD*+2ferricyanide→GOD+2ferrocyanide  reaction 2 where GOD is the enzyme glucose oxidase, and GOD* is the 'activated' enzyme. Ferricyanide ($[Fe(CN)_6]^{3-}$) is the 'mediator' which returns the GOD* to its catalytic state. GOD, an enzyme catalyst, is not consumed during the reaction so long as excess mediator is present. Ferrocyanide ($[Fe(CN)_6]^{4-}$) is the product of the total reaction. Ideally there is initially no ferrocyanide, although in practice there is often a small quantity. After reaction is complete the concentration of ferrocyanide (measured electrochemically) indicates the initial concentration of glucose. The total reaction is the sum of reactions 1 and 2:

reaction 3

$$\text{glucose} + 2\text{ferricyanide} \xrightarrow{\text{GOD}} \text{gluconic acid} + 2\text{ferrocyanide}$$

"Glucose" refers specifically to β-D-glucose.

The prior art suffers from a number of disadvantages. Firstly, sample size required is greater than desirable. It would be generally preferable to be able to make measurements on samples of reduced volume since this in turn enables use of less invasive methods to obtain samples.

Secondly, it would be generally desirable to improve the accuracy of measurement and to eliminate or reduce variations due, for example, to cell asymmetry or other factors introduced during mass production of microcells. Likewise, it would be desirable to reduce electrode "edge" effects.

Thirdly, since the cells are disposable after use, it is desirable that they be capable of mass production at relatively low cost.

DISCLOSURE OF THE INVENTION

According to one aspect the invention consists in a method of manufacture of an electrochemical cell comprising the steps of:

forming an aperture extending through a sheet of electrically resistive material, said aperture defining a side wall of the cell;

mounting a first thin electrode layer to one side of the sheet and extending over the aperture whereby to define a cell first end wall;

mounting a second thin electrode layer to the other side of the sheet and extending over the aperture whereby to define a cell second end wall in substantial overlying registration with the first electrode; and providing means for admission of a liquid into the cell defined between the side wall and said end walls.

The first and second electrode layers may be conductors or semi-conductors and may be the same or different. Noble metal electrode layers are preferred.

In preferred embodiments of the invention the aperture is of circular cross-section whereby the side wall is cylindrical and the first and second electrodes cover the aperture.

DESCRIPTION OF PREFERRED EMBODIMENTS

The invention will now be particularly described by way of example only with reference to the accompanying schematic drawings wherein:

FIG. 1 shows the product of manufacturing step 2 in plan.

FIG. 2 shows the product of FIG. 1 in side elevation.

FIG. 3 shows the product of FIG. 1 in end elevation.

FIG. 4 shows the product of manufacturing step 3 in plan.

FIG. 5 shows the product of FIG. 4 in cross-section on line 5—5 of FIG. 4.

FIG. 6 shows the product of manufacturing step 5 in plan.

FIG. 7 shows the product of FIG. 6 in side elevation.

FIG. 8 shows the product of FIG. 6 in end elevation.

FIG. 9 shows the product of manufacturing step 7 in plan.

FIG. 10 is a cross-section of FIG. 9 on line 10—10.

FIG. 11 shows the product of FIG. 9 in end elevation.

FIG. 12 shows a cell according to the invention in plan.

FIG. 13 shows the call of FIG. 12 in side elevation.

FIG. 14 shows the cell of FIG. 12 in end elevation.

FIG. 15 shows a scrap portion of a second embodiment of the invention in enlarged section.

The construction of a thin layer electrochemical cell will now be described by ay of example of the improved method of manufacture.

Step 1: A sheet 1 of Melinex® (a chemically inert, and electrically resistive Polyethylene Terephthalate ["PET"]) approximately 13 cm×30 cm and 100 micron thick was laid flat on a sheet of release paper 2 and coated using a Number 2 MYAR bar to a thickness of 12 microns wet (approximately 2–5 microns dry) with a water-based heat activated adhesive 3 (ICI Novacoat system using catalyst:adhesive). The water was then evaporated by means of a hot air dryer leaving a contact adhesive surface. The sheet was then turned over on a release paper and the reverse side was similarly coated with the same adhesive 4, dried, and a protective release paper 5 applied to the exposed adhesive surface. The edges were trimmed to obtain a sheet uniformly coated on both sides with tacky contact adhesive protected by release paper.

Step 2: The sheet with protective release papers was cut into strips 7, each about 18 mm×210 mm (FIGS. 1–3).

Step 3: A strip 7 of adhesive-coated PET from step 2 with release paper 2, 5 on respective sides, was placed in a die assembly (not shown) and clamped. The die assembly was adapted to punch the strip with a locating hole 10 at each end and with for example 37 circular holes 11 each of 3.4 mm diameter at 5 mm centres equi-spaced along a line between locating holes 10. The area of each hole 11 is approximately 9 square mm.

Step 4: A sheet 12 of Mylar® PET approximately 21 cm square and 135 microns thick was placed in a sputter coating chamber for palladium coating 13. The sputter coating took place under a vacuum of between 4 and 6 millibars and in an atmosphere of argon gas. Palladium was coated on the PET to a thickness of 100–1000 angstroms. There is thus formed a sheet 14 having a palladium sputter coating 13.

Step 5: The palladium coated PET sheet 14 from Step 4 was then cut into strips 14 and 15 and a die was used to punch two location holes 16 in each strip, at one end (FIGS. 6, 7 and 8). Strips 14 and 15 differ only in dimension strips 14 being 25 mm×210 mm and strips 15 being 23 mm×210 mm.

Step 6: A spacer strip 7 prepared as in step 3 was then placed in a jig (not shown) having two locating pins (one corresponding to each locating hole 10 of strip 7) and the upper release paper 2 was removed. A strip 14 of palladium coated PET prepared as in step 5 was then laid over the adhesive layer, palladium surface downwards, using the jig pins to align the locating holes 16 with the underlying PET strip 7. This combination was then passed through a laminator comprising a set of pinch rollers, one of which was adapted to heat the side bearing a palladium coated PET strip 14. The roller on the opposite side of the strip 7 was cooled. By this means, only the adhesive between the palladium of strip 14 and PET strip 7 was activated.

Step 7: PET strip 7 was then turned over and located in the jig with the release coating uppermost. The release coating was peeled off and second palladium coated strip 15 was placed palladium side down on the exposed adhesive surface using the locating pins to align the strips. This assembly was now passed again through the laminator of step 6, this time with the hot roll adjacent the palladium coated Mylar® added in step 7 so as to activate the intervening adhesive (FIGS. 9, 10 and 11).

Step 8: The assembly from step 7 was returned to the die assembly and notches 16 punched in locations so as to extend between the circular holes 11 previously punched in the Melinex® PET and the strip edge 17. Notches 16 extend so as to intercept the circumference of each circular cell. The strip was then guillotined to give 37 individual "sensor strips", each strip being about 5 mm wide and each having one thin layer cavity cell (FIGS. 12, 13 and 14).

There is thus produced a cell as shown in FIGS. 12, 13 or 14. The cell comprises a first electrode consisting of PET layer 12, a palladium layer 13, an adhesive layer 3, a PET sheet 1, a second adhesive layer 4, a second electrode comprising palladium layer 13, and a PET layer 12. Sheet 1 defines a cylindrical cell 11 having a thickness in the cell axial direction corresponding to the thickness of the Melinex® PET sheet layer 1 together with the thickness of adhesive layers 3 and 4. The cell has circular palladium end walls. Access to the cell is provided at the side edge of the cell where notches 16 intersect cell 11.

In preferred embodiments of the invention, a sample to be analysed is introduced to the cell by capillary action. The sample is placed on contact with notch 16 and is spontaneously drawn by capillary action into the cell, displaced air from the cell venting from the opposite notch 16. A surfactant may be included in the capillary space to assist in drawing in the sample.

The sensors are provided with connection means for example edge connectors whereby the sensors may be placed into a measuring circuit. In a preferred embodiment this is achieved by making spacer 1 shorter than palladium supporting sheets 14, 15 and by making one sheet 15 of shorter length than the other 14. This forms a socket region 20 having contact areas 21, 22 electrically connected with the working and counter electrodes respectively. A simple tongue plug having corresponding engaging conduct surfaces can then be used for electrical connection. Connectors of other form may be devised.

Chemicals for use in the cell may be supported on the cell electrodes or walls, may be supported on an independent support contained within the cell or may be self-supporting.

In one embodiment, chemicals for use in the cell are printed onto the palladium surface of the electrode immediately after step 1 at which stage the freshly-deposited palladium is more hydrophilic. For example, a solution containing 0.2 molar potassium ferricyanide and 1% by weight of glucose oxidase dehydrogenase may be printed on to the palladium surface. Desirably, the chemicals are printed only in the areas which will form a wall of the cell and for preference the chemicals are printed on the surface by means of an ink jet printer. In this manner, the deposition of chemicals may be precisely controlled. If desired, chemicals which are desirably separated until required for use may be printed respectively on the first and second electrodes. For example, a GOD/ferrocyanide composition can be printed on one electrode and a buffer on the other. Although it is highly preferred to apply the chemicals to the electrodes prior to assembly into a cell, chemicals may also be introduced into the cell as a solution after step 6 or step 8 by pipette in the traditional manner and the solvent subsequently is removed by evaporation or drying. Chemicals need not be printed on the cell wall or the electrodes and may instead be impregnated into a gauze, membrane, non-woven fabric or the like contained within, or filling, the cavity (eg inserted in cell 11 prior to steps 6 or 7). In another embodiment the chemicals are formed into a porous mass which may be introduced into the cell as a pellet or granules. Alternatively, the chemicals may be introduced as a gel.

In a second embodiment of the invention a laminate 21 is first made from a strip 14 as obtained in step 5 adhesively sandwiched between two strips 7 as obtained from step 3. Laminate 20 is substituted for sheet 1 in step 5 and assembled with electrodes as in steps 6 and 7.

There is thus obtained a cell as shown in FIG. 15 which differs from that of FIGS. 9 to 11 in that the cell has an annular electrode disposed between the first and second electrode. This electrode can for example be used as a reference electrode.

It will be understood that in mass production of the cell, the parts may be assembled as a laminate on a continuous line. For example, a continuous sheet 1 of PET could be first punched and then adhesive could be applied continuously by printing on the remaining sheet. Electrodes (pre-printed with chemical solution and dried) could be fed directly as a laminate onto the adhesive coated side. Adhesive could then be applied to the other side of the punched core sheet and then the electrode could be fed as a laminate onto the second side.

The adhesive could be applied as a hot melt interleaving film. Alternatively, the core sheet could first be adhesive coated and then punched.

By drying chemicals on each electrode prior to the gluing step the electrode surface is protected from contamination.

Although the cell has been described with reference to Mylar® and Melinex® PET, other chemically inert and electrically resistive materials may be utilised and other dimensions chosen. The materials used for spacer sheet 1 and for supporting the reference and counter electrodes may be the same or may differ one from the other. Although the invention has been described with reference to palladium electrodes, other metals such as platinum, silver, gold, copper or the like may be used and silver may be reacted with a chloride to form a silver/silver chloride electrode or with other halides. The electrodes need not be of the same metal.

Although the use of heat activated adhesives has been described, the parts may be assembled by use of hot melt adhesives, fusible laminates and other methods.

The dimensions of the sensor may readily be varied according to requirements.

While it is greatly preferred that the electrodes cover the cell end openings, in other embodiments (not illustrated) the electrodes do not entirely cover the cell end openings. In that case it is desirable that the electrodes be in substantial overlying registration.

Preferred forms of the invention in which the electrodes cover the apertures of cell 11 have the advantages that the electrode area is precisely defined simply by punching hole 11. Furthermore the electrodes so provided are parallel, overlying, of substantially the same area, and are substantially or entirely devoid of "edge" effects.

Although in the embodiments described each sensor has one cell cavity, sensors may be provided with two or more cavities. For example, a second cavity may be provided with a predetermined quantity of the analyte and may function as a reference cell.

As will be apparent to those skilled in the art from the teaching herein contained, a feature of one embodiment herein described may be combined with features of other embodiments herein described or with other embodiments described in our co-pending application. Although the sensor has been described with reference to palladium electrodes and a GOD/ferrocyanide chemistry, it will be apparent to those skilled in the art that other chemistries, and other materials of construction may be employed without departing from the principles herein taught.

What is claimed is:

1. An electrochemical sensor for analytic determination using a liquid sample, comprising a substantially flat strip having a thickness, the strip having at least two lateral edges, a sample-receiving cell within the strip, at least two electrodes in communication with the cell, and a notch through the entire thickness of the strip in at least one of the lateral edges thereof, wherein the notch is in fluid communication with the cell and allows entry of the liquid sample into the cell.

2. The sensor of claim 1, further comprising a vent in communication with the cell, the vent being adapted to allow air to escape the cell to facilitate entry into the cell by the liquid sample.

3. The sensor of claim 1, wherein the entry of the liquid sample into the cell occurs via capillary action.

4. The sensor of claim 1, wherein the sample-receiving cell comprises at least one reagent.

5. The sensor of claim 4, wherein the reagent comprises a catalyst, a redox reagent, or surfactant.

6. The sensor of claim 4, wherein the reagent comprises an enzyme.

7. The sensor of claim 4, wherein the reagent comprises a glucose oxidase.

8. The sensor of claim 4, wherein the reagent comprises ferricyanide.

* * * * *

(12) EX PARTE REEXAMINATION CERTIFICATE (5650th)
United States Patent
Hodges et al.

(10) Number: US 6,174,420 C1
(45) Certificate Issued: Jan. 9, 2007

(54) ELECTROCHEMICAL CELL

(75) Inventors: Alastair McIndoe Hodges, Blackburn South Victoria (AU); Thomas William Beck, South Windsor (AU); Oddvar Johansen, Mulgrave (AU); Ian Andrew Maxwell, Leichhardt (AU)

(73) Assignee: Lifescan, Inc., Milpitas, CA (US)

Reexamination Request:
No. 90/007,399, Jan. 27, 2005
No. 90/007,401, Jan. 28, 2005

Reexamination Certificate for:
Patent No.: 6,174,420
Issued: Jan. 16, 2001
Appl. No.: 09/314,251
Filed: May 18, 1999

Related U.S. Application Data

(63) Continuation of application No. 09/068,828, filed on Mar. 15, 1999, now Pat. No. 6,179,979, and a continuation of application No. 08/852,804, filed on May 7, 1997, now Pat. No. 5,942,102.

(30) Foreign Application Priority Data

Nov. 15, 1996 (AU) .............................. PCT/AU96/00723

(51) Int. Cl.
*G01N 27/26* (2006.01)

(52) U.S. Cl. ........................................ 204/403; 204/409
(58) Field of Classification Search ................ 204/403, 204/409, 411; 324/450
See application file for complete search history.

(56) References Cited

U.S. PATENT DOCUMENTS

| | | | |
|---|---|---|---|
| 4,088,448 A | 5/1978 | Lilja et al. | 23/259 |
| 4,654,197 A | 3/1987 | Lilja et al. | 422/56 |
| 5,120,420 A | 6/1992 | Nankai et al. | 204/403 |
| 5,312,590 A | 5/1994 | Gunasingham | |
| 5,437,999 A | 8/1995 | Diebold et al. | |
| 5,520,787 A | 5/1996 | Hanagan et al. | |

FOREIGN PATENT DOCUMENTS

| EP | 0 359 831 A1 | 3/1990 |
|---|---|---|
| EP | 0 359 831 B1 | 8/1995 |

OTHER PUBLICATIONS

EPO Communications re European Patent Application No. 99202305.1—Dec. 5, 2000: EPO Search Report & Annex (EPO Forms 1507.0, 1503, and P0459) (total pages: 3); Apr. 9, 2001: Communication pursuant to Article 96(2) EPC (EPO Forms 2001 and one page enclosure, EPO Form 2906) (total pages: 2); Jan. 16, 2002: Communication pursuant to Article 96(2) EPC (EPO Form 2001 and two page enclosure, EPO Form 2906) (total pages: 3); Jul. 3, 2002: Summons to Attend Oral Proceedings Pursuant to rule 71(1) EPC (EPO Form 2008.1 and three page enclosure, EPO Form 2906) (total pages: 4); Oct. 25, 2002: Result of Consultation (EPO Forms 2049A and 2036) (total pages: 2); Dec. 9, 2002: Minutes in accordance with Rule 76(4) EPC (EPO Form 2042 and six page enclosure, Form 2906) (total pages: 7); Dec. 9, 2002: Communication under Rule 51(4) EPC and Annex (EPO Forms 2004, 2056, and 2906) (total pages: 11).

*Primary Examiner*—Stephen Stein

(57) ABSTRACT

A method of manufacture of a thin layer electrochemical cell (FIGS. 12, 14) comprising the steps of:
  forming an aperture (11) extending through a sheet (1) of electrically resistive material, said aperture defining a side wall of the cell,
  mounting a first thin electrode layer (13) to one side of the sheet and extending over aperture (11) whereby to define a cell first end wall,
  mounting a second thin electrode layer (13) to the other side of the sheet and extending over aperture (11) whereby to define a second cell end wall in substantial overlying registration with the first electrode, and
  providing means (16) for admission of a liquid into the cell.

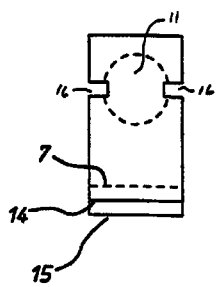

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 7 are determined to be patentable as amended.

Claims 2–6 and 8, dependent on an amended claim, are determined to be patentable.

1. An electrochemical sensor for analytic determination using a liquid sample, comprising a substantially flat strip having a thickness, the strip having at least two lateral edges, a sample-receiving cell within the strip, at least two electrodes in [communication] *direct contact* with the cell, and a notch through the entire thickness of the strip in at least one of the lateral edges thereof, wherein the notch is in fluid communication with the cell and allows entry of the liquid sample into the cell.

7. The sensor of claim 4, wherein [the reagent comprises glucose oxidase] *wherein said notch intersects the cell or wherein said liquid sample is in said notch*.

* * * * *